United States Patent [19]
Murry et al.

[11] 3,990,452
[45] Nov. 9, 1976

[54] MEDICAL MACHINE FOR PERFORMING SURGERY AND TREATING USING ULTRASONIC ENERGY

[75] Inventors: Edward J. Murry, Palos Park; Joseph F. Brumbach, Niles, both of Ill.

[73] Assignee: Fibra-Sonics, Inc., Chicago, Ill.

[22] Filed: June 13, 1975

[21] Appl. No.: 586,545

[52] U.S. Cl. .............................................. 128/305
[51] Int. Cl.² .................. A61B 17/32; A61H 23/02
[58] Field of Search ........................... 128/24 A, 305

[56] References Cited
UNITED STATES PATENTS

| | | | |
|---|---|---|---|
| 2,990,616 | 7/1961 | Balamuth et al. | 128/24 A UX |
| 3,086,288 | 4/1964 | Balamuth et al. | 128/305 UX |
| 3,584,327 | 6/1971 | Murry | 128/24 A X |
| 3,589,363 | 6/1971 | Banko et al. | 128/24 A X |
| 3,924,335 | 12/1975 | Balamuth et al. | 128/24 A X |

*Primary Examiner*—Channing L. Pace
*Attorney, Agent, or Firm*—Hill, Gross, Simpson, Van Santen, Steadman, Chiara & Simpson

[57] ABSTRACT

A machine for performing surgery and treatment utilizing ultrasonic energy wherein so as to obtain precise control of the operating frequency and eliminate unnecessary heating and loss of power the hand tool as well as the generator and power supply are designed after establishing the designed criteria of the particular medical tool required thus allowing coupling of energy into the tool in a very efficient manner. Means are also provided for assuring that dangerous transverse modes of the instrument used will not occur which can cause injury to patients. Several unique additional safety and construction features are also shown.

34 Claims, 35 Drawing Figures

MEDICAL MACHINE FOR PERFORMING SURGERY AND TREATING USING ULTRASONIC ENERGY

BACKGROUND OF THE INVENTION

1. Field of the Invention

This invention relates in general to medical machines for performing surgery and treatment utilizing ultrasonic energy and in particular to a novel ultrasonic operating unit.

2. Description of the Prior Art

Biological effects were achieved accidentally with ultrasound by Langevin who made "fish-kills" around 1922 with military sonar which destroyed tiny fish if they swam into its field. Records show that these tiny particles of tissue were probably captured in a low sonic pressure "well" and that their body cells were over-heated by the beam, causing their death. Other historical events germane to this field were:

An early mention of the use of ultrasonics in medicine appears in, "Der Ultraschall in Der Medzin" by Verlog S. Hirzel, Zurich, 1949, mostly in diathermy work.

A direct demonstration of the technology of irrigation, aspiration and ultrasonics to effect cure was done by Soviet scientists working on cancer. The work obtained astonishing results whereby the ultrasound "seemingly" exhibited or prevented the growth of cancer cells in tumors. Not only that but the cells when transplanted failed to set-off cancer in the new host, i.e. the treated animal was not only healed but became immune. The Soviet research used "Liquidation Resolution" i.e. ultrasonic emulsification. This report was made in 1956 yet little work has been done in the U.S.A. mostly due to lack of equipment.

A rather interesting historical article appeared in "Ultrasonic News" of Dec. 1957 on "Ultrasound in Medicine". In the article it states that "thru years of usage by thousands of medical investigators and million of treatment of patients is has been established that over 3 watts per sq. cm or a total of 15 watts may be, in some manner, hazardous and that power below this level is always safe". In the same article excellent results using ultrasound are reported for contusions, distortions, inflammatory skin lesions, stomach ulcers, warts, leg ulcers and scleroderma as well as other diseases. This article also reports that over 3,000 medical papers on the use of ultrasound in medicine were published by 1956.

This same magazine (Ultrasonic News) in January 1958 P. 31 states "Hundreds are presently working in chemical research developing new techniques and methods of ultrasonic applications," and later, "In each of the medical specialties there is considerable investigation; particularly, specific studies in the field of urology, cardiology, and work on certain disorders of the eye and ear".

In May 1962 Topp & Eisenklam set forth the usage of ultrasonic high power for medical atomizers and one design used 40 Khz and 25 watts of input power and an injection through the center for the inlet of liquid for irrigation.

A little known use of the direct application of ultrasonics to tissue is in the treatment of the rare disease of laryngeal papillomatosis which is the only way to preserve life of the diseased victims (Birck & Manhart), (1963). The ultrasonic application is the only known cure.

The Acta Anaesth. Scandinavia, Vol. 8, 1964, P. 49 Herzog et al, reports the use of ultrasound for "Humidification of inspired gases via aerosols".

In the journal called "Ultrasonic", edition of July 1967, a complete description of a machine and probe for treatment of Meriere's disease is set forth. The work was done at Upsula, Sweden by S. J. Johnson. The author claiming usage for 5 years (back to 1958).

In "Ultrasonic, the Low and High Intensity Application" by Ensminger (Marcel Derker, Inc., N.Y.) 1975, Ensminger states on P. 143 under 'Surgery', that "There is very little equipment in the market for surgical use. Small hand held transducers are available for removing dental calculus. A similar instrument can be obtained for use in cataract surgery for emulsification and removing the fluid in the lens".

In Japan records from 400 A.D. are available and in fact the actual instruments of the Majima period of Japan are available for cataract work. This particular device consisted of a fine tubular needle which went into the soft cataract in the eye, and a suction tube attached to it which was sucked on by the mouth. The data and equipment are at the Nagoya University in Japan (Hurad).

This truly ancient application of cataract irrigation and aspiration was not duplicated in the West much before 1676–1743, by Brisseau (published in 1709). By 1755 Jacques Dairiel originated the full irrigation-aspiration surgical knife technique, followed by Graefe, with his famous, still in use, Graefe Knife in about 1860. As early as 1952 Fuchs made use of a two needle technique to simultaneously irrigate and aspirate during cataract removal.

The next advances in cataract surgery took place in several places at once: in Russia, Japan, England and the U.S., with the most concerted scientific attack being that of Y. Kuwahara and his associates in 1942 during the difficult war period and several years thereafter (until 1952). In 1952 Lavine et al, published "Effects of Ultrasonic Waves on the Refractive Media of the Eye" (Arch. Ophth. 47-204-1952), while at the same time Bergran, et al, in his "Ultrasonics and Their Scientific and Technical Application:" (Edward Buss, 3rd, Edition, Ann Arbor, 1942) pointed out the first early use of ultrasonics for medical work.

Examples herein of precedent devices clearly shows that the prior art used ½ wave vibrating stacks of nickel alloy material—the vibrations being created by the imposition of a high frequency magnetic field—to which has been attached a tool tip of one sort or another for doing surgical work. In most cases, the ultrasonic vibration was first laboriously created, and the knife, needle, saw, et al, was then "stuck-on", almost as an afterthought. The power was then applied and high frequency vibrations achieved—at only 2 to 10% efficiency. Thus, it is common practice to use 20 to 60 watts of instrument input power in dental scalers, when the job can be done with 10 watts or less and with far superior effectiveness if the device is designed as a system for effecting a specific task.

Even if prior inventors had fully recognized the need to make the tool element (i.e. the instrument used) part of the vibrating system, this would have usually been rendered impossible by the preexistant tools shape itself—which they insisted on using—the tool material chosen, or the operating length of the tool required to get ultrasonic energy into the work area; which did not match the ultrasonic requirements.

Thus, in the past too much compromise has been made in an effort to "make do", or to simply get any amount of ultrasound to work; with the result that most ultrasonic devices used in medical work are ineffective, inefficient and too difficult to use —when they work at all.

In the presentation of the invention which follows, we will show how devices can be evolved which will meet the criteria of the desired work problem uniquely; therefore, the object of this invention is to describe the complete electromechanical system, and its parts, and to show how to apply principles of ultrasonic design which are new and revealed herein for the first time.

In the "Fundamental Studies of Phaco-Emulsification" (Sect. VII: Y. Kuwahara, et al) the prevailing state of the ultrasonic medical art prior to our invention is epitomized in the drawing on Page 49 FIG. 38, however, this same approach is also shown in numerous texts on ultrasonic transducers, horns and tools of every sort and is here briefly shown, in FIGS. 1A and 1B.

Figure 1A:
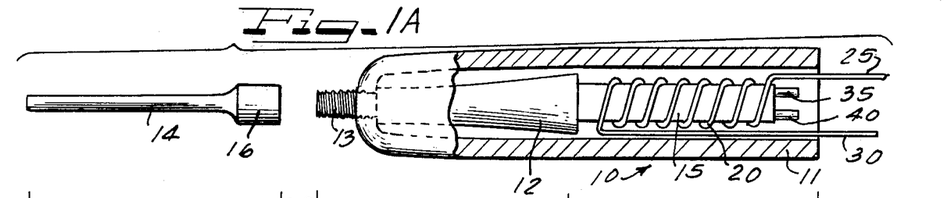
FIG. 1A illustrates the state of the art for straight, hand held instruments (Comes apart at λ/2 wave point.).
Figures 1B, 2A, 2B, 2C:
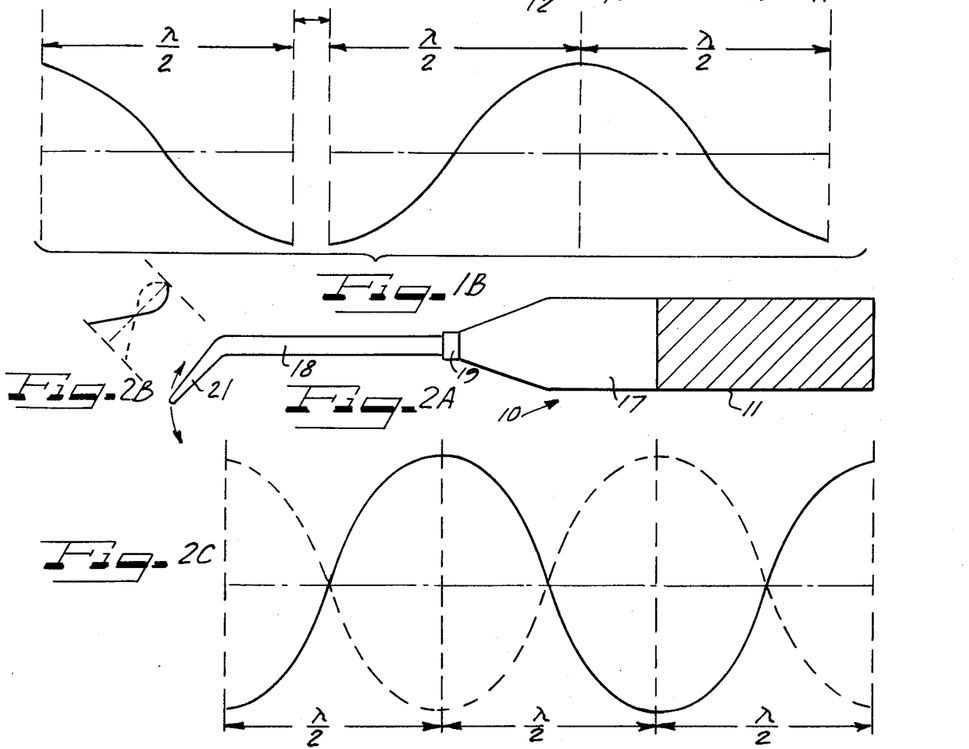
FIG. 1B is a plot of vibratory amplitude against physical distance of these state of the art instruments.
FIG. 2A illustrates a curved-end state of the art workpiece, (Does not come apart.).
FIG. 2B illustrates the lateral motion of the tip head-on of the workpiece in 2A.
FIG. 2C is a plot of vibratory amplitude against physical distance, including only part of tip of curved workpiece.

In FIGS. 2A, B and C are shown an "idealization" of the "bent-needle" approach as visualized by Kuwahara and Associates. Note the assumption that the ultrasonic wave bends around the corner readily and the lack of any mismatch depiction at the joint; two conditions which are exactly never true.

SUMMARY OF THE INVENTION

The present inventors having been well aware of the use of ultrasonics for dental plaque removal cataract break-up, homogenization of cells, haemolysis, lesion production, cell disruption in tissue, breaking of kidney stones, etcetera, and having thoroughly realized the need for improved equipment an extensive effort was begun to first better understand the several phenomenon involved and to devise a superior machine for doing all of these medical tasks more safely, much more effectively and at a far less cost than devices of the prior art. Furthermore, it was decided to design such a machine from a "Doctors Eye View", i.e. for maximum safety, ease of use and flexibility in the operating room, and effectiveness. A medical machine of such an invention would need have the following criteria:

It must be safe under all possible conditions, viz:
a. It must be explosion proof.
b. It should indicate by all means possible (i.e. visual, tactile and sonic) when it is on.
c. It should be completely sterilizable by at least gas technology and preferably by flash autoclaving.
d. It should have multiple, redundant electrical grounds and a fail/safe indicator if a ground return is lost.
e. It should be Underwriter Laboratory and F.D.A. approved.
f. It should have simple, error-free indication of power output and use an absolute minimum of power at all times.
g. It should incorporate all known safety features.
h. It should provide ultrasonic energy to surgeons, for whatever purpose required, in a neat, clean reasonably priced package.
i. It should be available for sale to doctors in a usable form and should be well tested and market-proved.
j. It should be effective when used.

The present invention meets these criteria to a very high extent and works very efficiently and effective as compared to existing devices.

The largest single area of missing ultrasonic medical knowledge at present is in the area of the physical application of the high frequency vibrations to the actual workpiece—the instrument piece by which work is to be done; i.e. from which energy is then transferred to the work itself. In this area far too little efforts has been actually done, yet hundreds of patents now exist on devices proporting to do A or B, but which fails to do A or B because the ultrasonic energy available is not actually being put into the work piece, (let alone into the work) or only in a small inefficient amount.

Specifically, although for over 30 years much talk and written matter has occurred on the use of ultrasonic medical tools, few real tools are available for actual sale and use by doctors in their daily practice—which conclusively demonstrates the obvious futility of the patents and work effort so far. Practically, the sole exceptions to the rule of "Talk, but no reality", is the dental scaler, which does a fairly excellent job, in spite of its apparent super-high inefficiency. It is somewhat effective but not efficient. This is due mostly, and simply, to the misunderstanding of the critical nature of the mechanical design problem involved and the sonic complexity of the electromechanical problem, with its inherent electronic "phasing" problem. These problems exist for all ultrasonic instrumentation systems. Our efforts have been directed specifically towards reducing the amount of ultrasonic energy used in medical operations and toward the achieving of superior safety, efficiency and effectiveness. Our machine was required to be simpler, more reliable and less costly than several already in use in specific areas, such as for cataract removal or tooth scaling as well as safe to use anywhere.

The present invention relates to such a specific ultrasonic medical system which was designed for a specific task and which makes use of a consistant and scientific design approach, resulting in a unique, highly effective, efficient, electromechanical set-up able to be used with a minimum of effort by surgeons, in safety and full confidence.

Other objects, features and advantages of the present invention will be readily apparent from the following detailed description of certain preferred embodiments thereof, taken in conjunction with the accompanying drawings, although variations and modifications may be effected without departing from the spirit and scope of the novel concepts of the disclosure and in which:

DESCRIPTION OF THE PREFERRED EMBODIMENTS

FIG. 1A illustrates an ultrasonic device 10 of the prior art having a hollow metal or plastic outer case 11 in which a vibrating motor transducer 15 is mounted with its front end connected to a transition horn 12 with a threaded portion 13 to which the needle 14 was connected by threaded coupling 16 which mates with the threads 13. FIG. 1B illustrates the vibrational amplitude vs. physical distance characteristic of all devices similar to FIG. 1A. FIG. 2A illustrates a form of the device having a curved needle 18 with a curved tip 21 which undesirably vibrates sideways in a transverse motion as shown by the arrows. FIG. 2B illustrates the motion of the tip 21 while FIG. 2C illustrates the distance vs. amplitude characteristic of the rest of this configuration. Rozenberg in his book entitled "Sources of High Intensity Ultrasound Volune II" proves that the supporting point of the internal motor 15 shifts with external loading and, thus, with the prior art devices of FIGS. 1A and 2A energy is severely lost due to the metal or plastic case attaching arrangement and further uncomfortable and perhaps dangerous vibrating energy is coupled into the hands of an operator utilizing these instruments, as the mounting point shifts under load.

The previous art's motors (FIG. 1A) may comprise a supporting outer metal or plastic tube 11 in which a nickel/steel magnetostrictive driver 15 is mounted and which has a coil 20 with energizing leads 25 and 30 to which suitable power is supplied and which has cooling passages 35 and 40 for liquid cooling the device by circulating.

Figure 3A:
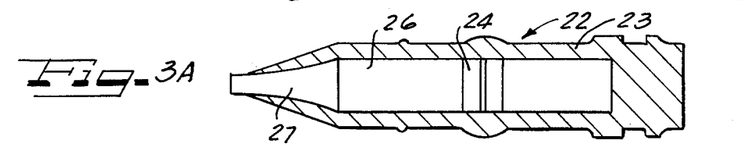
FIG. 3A illustrates the basic form of the present invention for one single frequency.
Figure 3B:
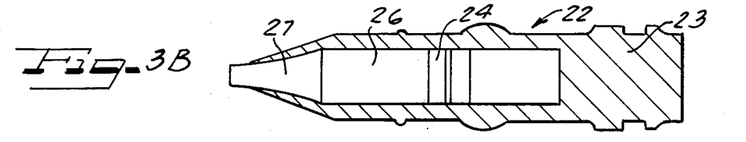
FIG. 3B illustrates the basic invention for a higher frequency different from the device of FIG. 3A. (Note shortening of motor.)
Figure 3C:
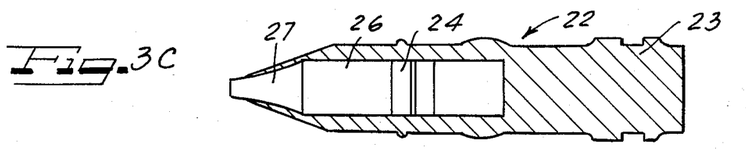
FIG. 3C illustrates the basic invention for yet another still higher frequency (Again, note still more shortening of motor.).

FIGS. 3A, 3B, 3C, 4A and 4B illustrate the device of the present invention which is completely encapsulated such that the entire handpiece is surrounded by molded rubber, as for example, RTV type rubber molded onto the motor as a single jacket piece. The rubber 23 surrounds the driving crystals 24 and FIGS. 3A, 3B and 3C illustrate handpieces of the same physical size but designed for difference increasingly high frequencies. The front part of the motor 26 is directly coupled to a geometric transition horn 27 as shown.

Figure 4A:
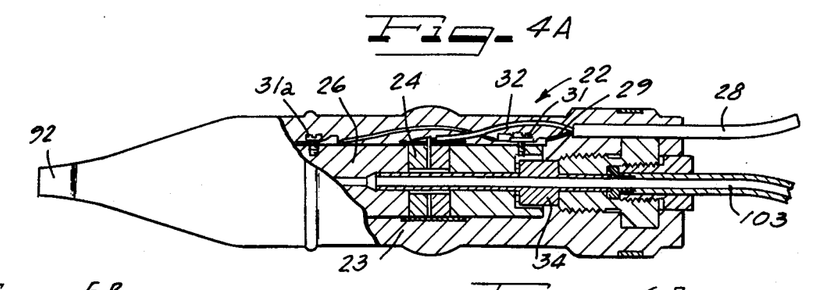
FIG. 4A illustrates an actual operating tool-piece of the invention showing full construction details.

FIG. 4A is a partially cut-away view of the invention illustrating a cable 28 including a copper shield 29 which is connected to the motor rear piece by screw 31. The voltage lead 32 is connected to the back-to-back crystals. In addition, a loosely knit shield (FIG. 4C) 29a is formed about the cable 28 and provides a very special high ohmage second ground to the motor by screw 31A. This redundant ground can preferably be fabricated of stainless steel so as to provide abrasive protection, good flexibility and allow the unit to be sterilized in an autoclave as well as the high resistance. The second shield (29a) over 28 must have resistivity of approximately 8.ohms from the handpiece 22 to the safety ground plug 28B provided on the control unit 105 since in the event of failure of the main ground 29 anywhere in the handpiece the secondary safety ground (29a) provided over the conductive cable 28 merely cuts down the power to the handpiece 22 still maintaining the safety of the circuit but preventing any further medical work with the probe due to its then lower unworkable power output. This will automatically require the operator using the handpiece 22 to change handpieces before proceeding with an operation.

Figures 5A, 5B:
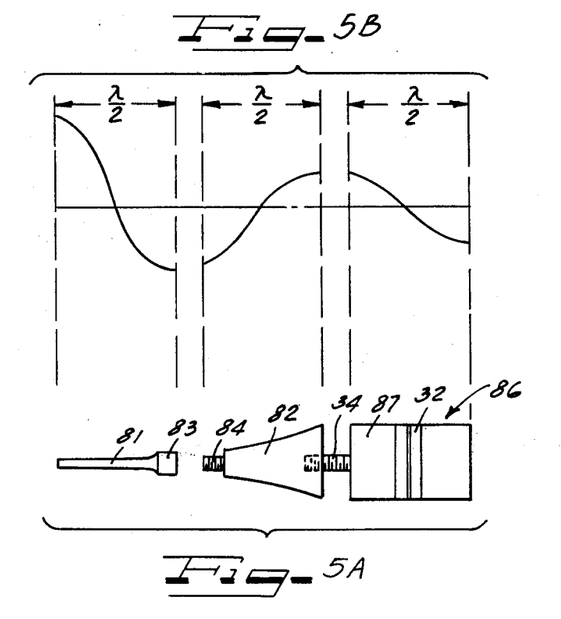
FIG. 5A is a view of an earlier version of the invention Before full understanding was achieved, it, too, "broke" the tool at a vibrating antinode (a ladon).
FIG. 5B is a plot of vibratory amplitude against physical distance for the earlier invention. Note, the use of 3 half-waves in a typical manner, making the working tip act "lossy."

The needle 33 of the invention must be constructed with extremely high precision and case. The needles are sample X-rayed, sonically cleaned and sonically tested before being put to use. The motor and horn may be advantageously mechanically prebiased by the center bolt 34 such as illustrated in FIG. 4A and 5A and since the needles and cannula may be stressed up to 85% of their tensile strength at the full power-level input as documented in the data books for each gauge of tubing utilized, the entire motor/horn crystals can also afford to be prebiased to 85% of the maximum tensile strength of the hollow titanium center lock-up bolt 34 with great advantage to safety and effectiveness.

For the design of a motor (transducer) to be driven by an electrical generator and which will then convert the electrical energy into mechanical vibratory energy, the following equations are important and are well known in the art:

$$I = \frac{\rho v}{2} = \frac{p^2}{2\rho v} = \frac{\rho c v^2}{2}$$

Where $\rho$ is the density of the material being utilized, $c$ is the velocity of sound in the material being vibrated, $p$ is the sound pressure, $v$ is the particle velocity, and $I$ is the energy intensity of the wave front.

Thus it is seen from these equations that in order to achieve the high pressures needed dense materials moving at high velocity, in other words, metals and dense ceramics (PZT'S) are needed which means that the acoustic impedance $\rho c$ should be made high. Transferring power from the motor to other substances gives rise to a mismatch problem as, for example between air, water, animal tissue and metal, et al.

The acoustic impedance ($\rho c$) in $\mu$ bars/cm/sec for air is 42, while water is 151,000 and metals have a value of 4,500,000. Animal tissues varies with density and the velocity of propagation of sound through them but in general fall in the range between that for water and metal and might be, for example, about 980,000. For this reason, the transfer of vibratory energy to animal tissue can best be accomplished by direct contact or by the use of water or oil couples. Air is a very poor and very inefficient medium for transferring acoustic energy into tissue for various reasons.

For these reasons, it is desirable to irrigate at all times and to use low density metals or plastic on the input tip of the instrument, (i.e. cannula). Since frequencies which are high such as 30,000 cps or higher are utilized, a short physical wavelength with a rapid period of oscillation will result as shown by the following equation:

$$\lambda = c/f$$

where $\lambda$ is the wavelength, $c$ is the velocity of transmission in the motor and $f$ is the frequency of the vibrating energy input.

The equation clearly shows that once a frequency is selected the length of the vibrating motor is uniquely determined. Further, the acceleration and velocity of the vibrationally stressed material will be extremely high approaching the available materials strength limits.

For example, if the amplitude equals $A \sin \omega t$", the velocity equals $\omega \delta$ and acceleration is $\omega \delta^2$ and if, at 30 KHz $\omega$ is equal to $1.9 \times 10^5$ radians per second for example and if sufficient power is supplied to move the tip only 20 microns ($2 \times 10^{-5}$M), the velocity and acceleration will respectively be 3.8 meters per second and $7.2 \times 10^5$ meters per second$^2$. This value of acceleration is equal to 72,000 G and at such acceleration the at-rest inertial forces of all tissues would be sufficiently greater than required for needles or knives to penetrate completely, and even soft tissue and liquids would indeed stay in place and be so penetrated, and indeed are.

Hence, it is seen that in medical applications it is necessary to select superior tensile strength in the materials used in the motors and to utilize superior bonding and brazing techniques so as to permit the use of the higher powers resulting in the high G forces required if results are to be achieved.

Also, it is to be noted that at these extremely high G forces with the resulting acceleration of $7.2 \times 10^5$ meters per second normally plastic and semi-plastic materials behave like rigid bodies and shearing of semi-solid or gelid materials can and will occur in a manner similar to that in liquids disclosed in Murry U.S. Pat. No. 3,614,069. The necessary disparity occurs between the time of displacement and the time of recovery wherein the time of the displacement exceeds the time of recovery such that the elastic body cannot return to rest before shearing occurs. It does not matter whether the tissue is rigid and the longitudinally driven tip is moving extremely fast or whether the tip is rigid and the tissue is impelled against the tip very fast. Once the particle velocities become very high, non-rigid bodies can penetrate normally rigid bodies with ease and vice-versa; an example being the jet innoculator used for medical immunization.

Another phenomenon here which must be considered is: if sufficient intensity of radiation leaves a vibrating surface such as the tip of a needle or an osteotome into a fluid a cavitation threshold will occur in the fluid or semi-solid at some level. This is usually at 0.5 w/cm$^2$ in blood and 0.1 to 2.0 w/cm$^2$ in gelid tissues. For utilizing the cavitational phenomenon created by ultrasonic energy there must be impurities or gas micro-bubbles present and the power level must be then sufficiently high to effect "diffusion rectification" as described in Murry U.S. Pat. No. 3,614,069.

Still a third often neglected phenomenon has been discovered to be important to this work and which appears as a most important force available when high intensity ultrasound is present and which has been entitled "Micro Streaming". In the initial stages of our research this force was ignored as unimportant to tissue dissolution. After further work and intense, difficult experimentation, however, we now believe microstreaming to be the main force required in micro-surgery, cataract dissolution and cell disruption. For a detailed discussion reference may be made to the article by "Nyborg" entitled "First International Symposium On Ultrasound", Page 124–135. (17–19 September 1970).

We have discovered that micro-streaming and its proper use is critical to obtaining superior fragmentation, cavitation and liquifaction of tissue including cataract material. It has further been discovered that the angle of "grinding" of the ends of the needles and rods utilized is quite critical for the various tubing gauges and shapes used since it affects the working of the micro-streaming.

Figures 11, 12, 13, 14, 15:
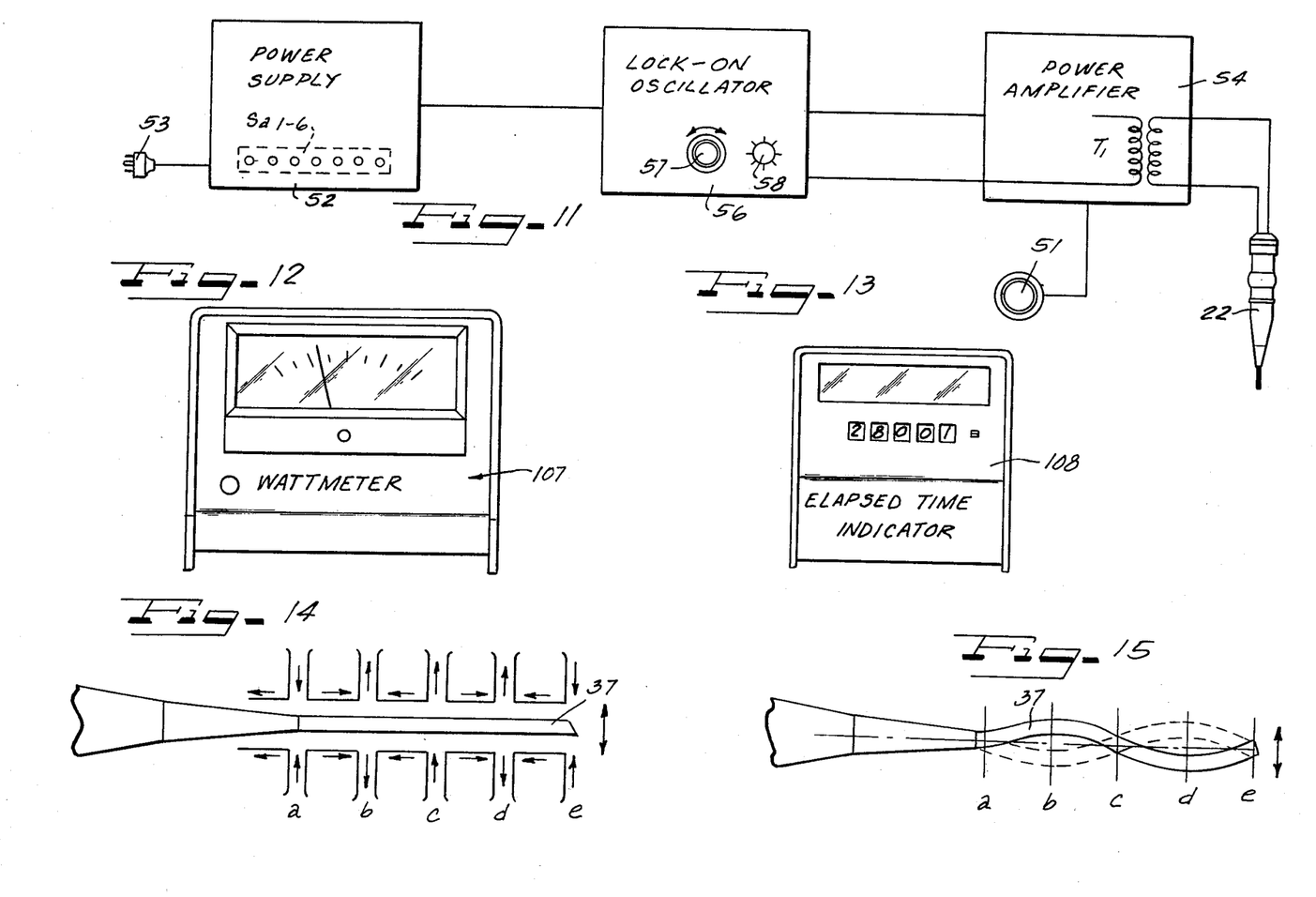
FIG. 11 is a simplified block diagram of the invention.
FIG. 12 illustrates a true reading high frequency interating wattmeter which gives true ultrasonic power into the workpiece, and which can be directly connected to the invention.
FIG. 13 illustrates an elapsed time indicator, also directly connectable for reading total exposure time of the tissue to the ultrasound.
FIG. 14 illustrates the microstreaming phenomenon along the surface of a rod, transversely and improperly vibrated. Little energy leaves the tip longitudinally.
FIG. 15 illustrates the actual incorrect movement of a transversely vibrated rod (needle creating incorrect energy input to tissue.

FIG. 14 illustrates micro-streaming along the length of a wire vibrating in a transverse mode, and FIG. 15 also illustrates a depiction of a wire vibrating in a transverse mode. (greatly exaggerated) which causes this type of microstreaming.

Figures 16, 17, 18, 19, 20:
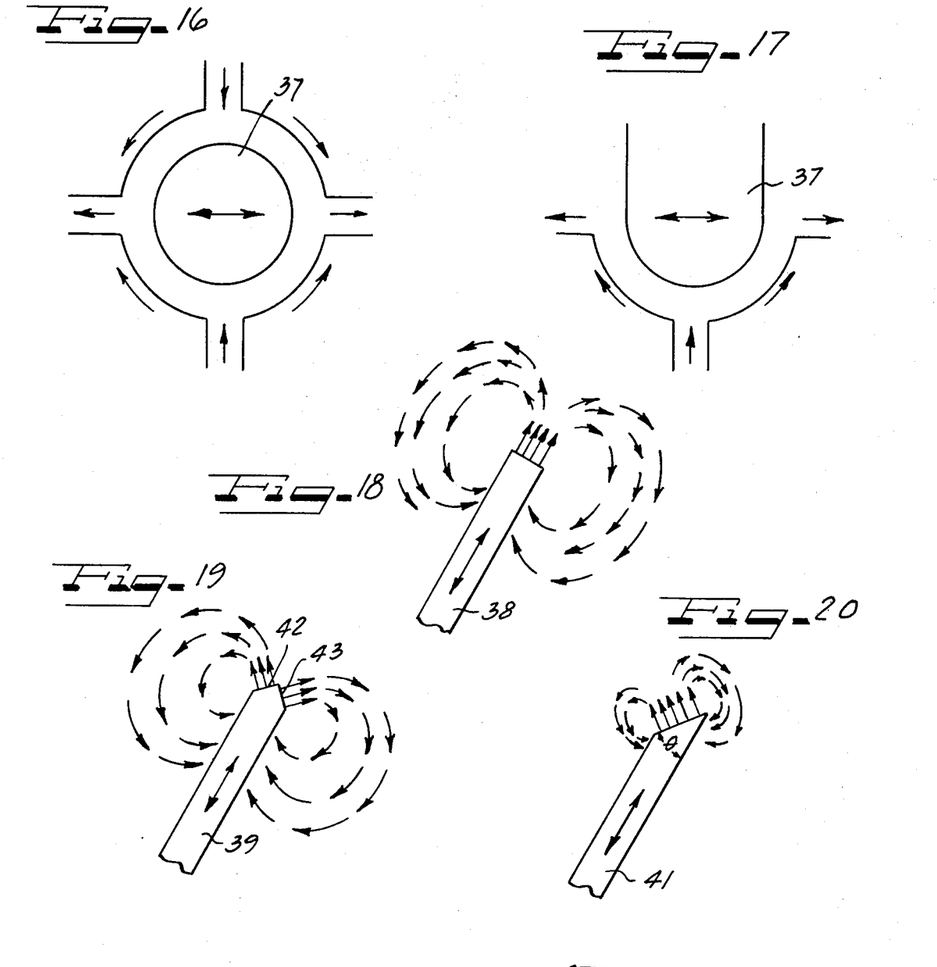
FIG. 16 illustrates microstreaming at the end face of a typical round rod also with improper transverse vibrations, showing ineffectiveness, since energy is around the rod.
FIG. 17 illustrates side-view microstreaming at the tip of a curved round rod, also improperly transversely vibrated, still showing ineffective energy transfer, but some energy does move into the tissue.
FIGS. 18, 19 and 20 illustrate variation in "proper" microstreaming from the tip of a truly longitudinal vibrated solid needle at different angles of "grind-off" Note, energy leaves the tip into the tissue, always returning. and, FIG. 21 illustrates a hollow needle ground off at the correct invention angle and shows the method of capture of broken fragments in a microstreaming "pool" for superior processing.

FIG. 16 illustrates an end view of a plain wire 37 with micro-streaming as it appears at the end of the wire when vibrating in an undesired transverse mode (left to right) and FIG. 17 illustrates a rounded tip of a rod transversely vibrated and the associated type of ineffective micro-streaming. Under longitudinal vibration as illustrated in FIGS. 18, 19 and 20 new effects become apparent. FIG. 18 illustrates micro-streaming with a square ended wire or rod 38 while FIG. 19 illustrates a wire or rod 39 with two 45° angles formed at its tip to form the radiating surfaces 42 and 43, respectively, so as to give an effective micro-streaming pattern illustrated in FIG. 19.

Figure 21:
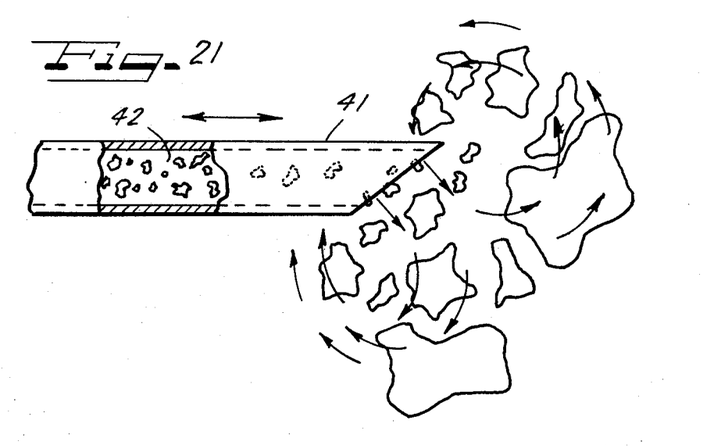

In FIG. 20, the wire or rod 41 has been cut so as to have a tip angle theta ($\theta$) as shown in the range between 30° and 40° and preferably at an exact angle of 37½° to obtain the highly advantageous circulating micro-streaming pattern illustrated in FIG. 20. FIG. 21 is an enlarged view illustrating a hollow needle rod ground to an angle of 37½°. As shown the solid particles being broken-up will become entrapped at this precise angle in the swirling small eddies illustrated and will be continuously and repetitiously exposed to the extremely intense sonic energy at the outermost tip of the needle 41. As the trapped fragments swirl and circle they become tinier and tinier due to the ultrasonic energy continuously acting on them until they become small enough such that they can be easily withdrawn through the center bore hole 42 of the needle as shown in FIG. 21 which is under continuous negative pressure. It is to be noted that by using an angle of 37½° the existant microstreaming energy will all be perpendicular to the 37½° radiating surface and that a large processing surface, in other words, a large annular area of high intensity ultrasound will exist and once the particle is captured in the micro-streaming's three dimensional volume pool it will be rapidly reduced in size by this continuously applied energy and will soon be completely emulsified by the heavy liquifying forces present. We have invariably observed how these particles become trapped and are forced to swirl and dance and quickly decrease in size and can then be readily withdrawn through the needle to be carried away. This process works on all types of tissues which have been tried including everything from fatty tissues to bone. While the high speed fragmentation may be caused by the super high velocities of the vibrating tool tip the dissolving of the tissues must be done by a non-shock wave phenomenon since shock waves cannot act on soft compliant surfaces. Hence, micro-streaming appears to be the primary cause of dissolution here.

FIG. 11 is a block diagram of the system illustrating a power supply 52 which receives primary power through an A.C. line power plug 53 and which supplies power to a unique lock-on oscillator 56 which has a tuning control 57 for varying the oscillator frequency and a tuning indicator 58. The output of the oscillator is supplied to a power amplifier 54 which is controlled by a foot switch 51 to couple power to the transducer 22 through the transformer T1.

Figure 8:
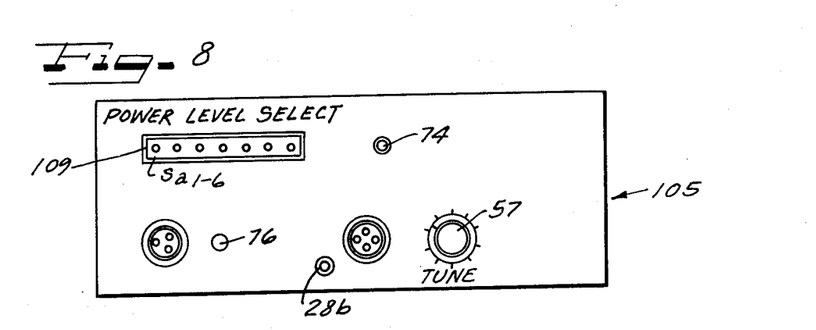
FIG. 8 is a view of the front panel showing the simplified controls of the invention.
Figure 9:
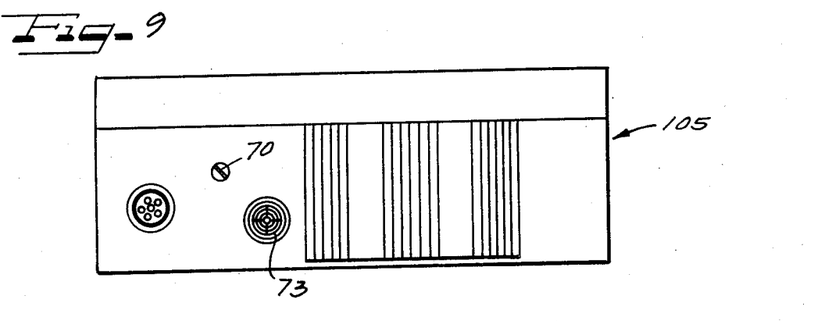
FIG. 9 is a rear view showing the tone level control of the invention and the plug for attaching extra devices.
Figure 10:
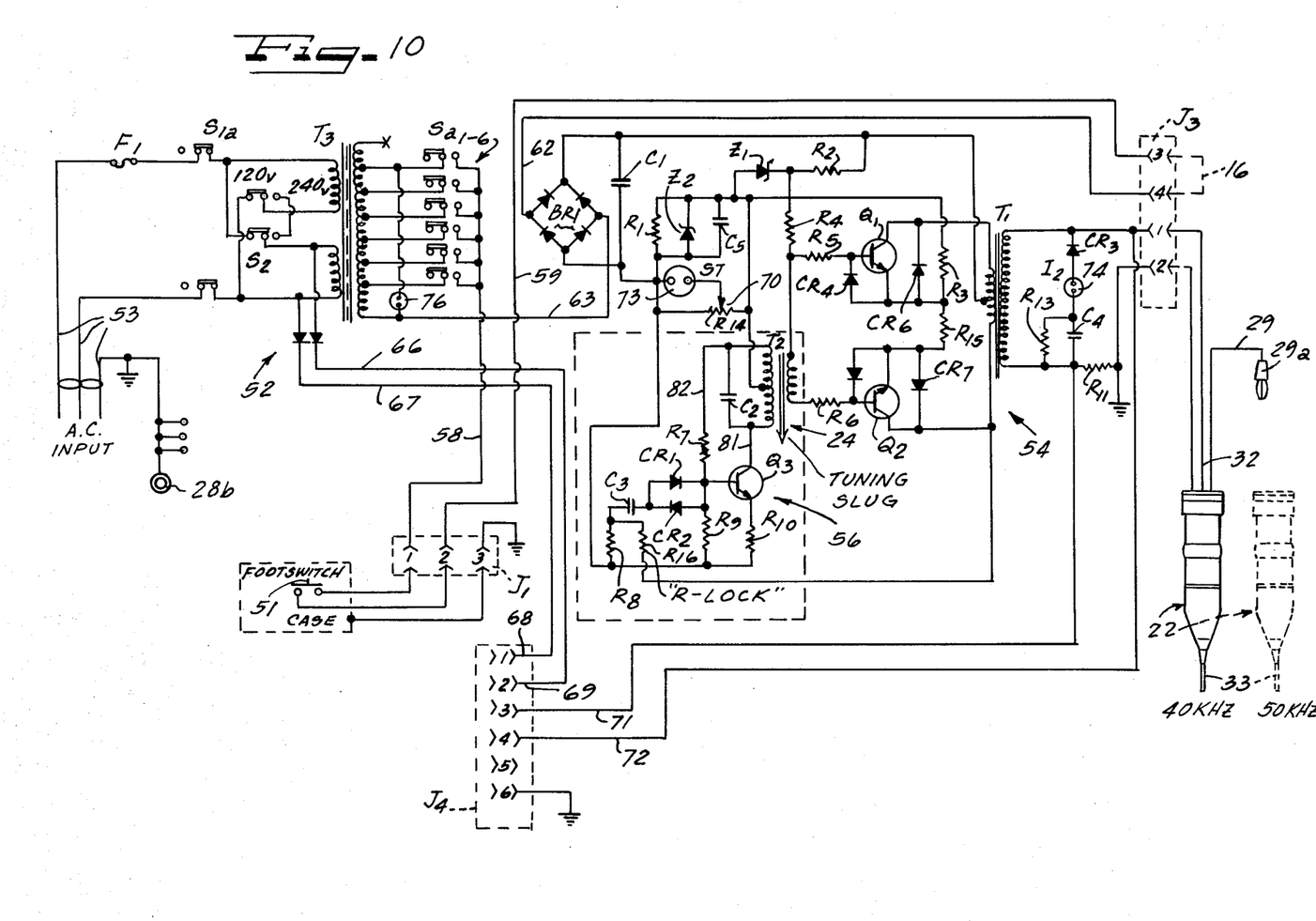
FIG. 10 is an actual electrical schematic of the invention, showing all features, and making full disclosures. Note: The unique power pushbutton control.

FIG. 10 is an actual electrical schematic of the power supply 52 the lock-on oscillator 56 and the power amplifier 54. The power supply 52 has a transformer T3 with its secondary tapped to provide 6 output voltages across the switches Sa 1 through 6. Thus, power supplied through lead 58 to the foot switch 51 can be arranged so as to provide 2.5, 5.0, 7.5, 10.0, 12.5 and 15.0 watts output power to the handpiece 22 depending on the position of the push-button switch Sa1 through 6. The transformer T3 is electrically shielded and the switch contacts can be completely sealed by potting and by installing a gas-proof rubber booth 109 into the front panel. This permits ease of switching and also permits complete gas proofing. The power output lead 59 of the foot switch 51 is connected to a terminal of connection block J3 which has a power interlock 61 for supplying power on lead 62 and 63 to the bridge BR1 so as to provide rectified power across the capacitor C1. A true reading watt meter 107 as illustrated in FIG. 12 can be connected to terminals 68 and 69 of plug J4 which are connected to power leads 66 and 67 across the primaries of transformer T3. The watt meter is also simultaneously connected to leads 71 and 72 to measure the power supplied to the hand probe 22. When the foot switch 51 is depressed a buzzer 73 mounted on the rear panel of the unit can be set to any level of audible sound indication desired by its rear control 70 and when the foot pedal switch 51 is depressed the ultrasonic output will be supplied to the hand probe 22 and the buzzer 73 will be energized and a power output indicator tuning light 74 on the front of the unit as illustrated in FIG. 8 will be turned on. An A.C. power-on light 76 on the front panel indicates when light power is supplied to the unit and the switches Sa1 through 6 allow the desired power level to be set.

Once the foot switch 51 is closed the handpiece 22 is turned by rotating a tuning knob 57 which moves the inductor tuning coil of transformer T2 until the tuning light 74 indicates a "dimming" of resonant condition. Thus, the operator has merely to plug in the handpiece 22, the foot switch 51 and the line cord plug 53 and adjust the tuning knob 57, (FIG. 8) until the tuning indicator light 74 dims and the machine is ready to be used in an operation. The only other adjustment for the device is the level of audible sound adjustment 70 on the back of the unit so as to set the audible buzzer level desired.

In the circuit diagram the oscillator transistor Q3 is the heart of the oscillator 56 and its output feeds the primary lead 81 of transformer T2. Feedback is supplied to the oscillator through lead 82 from the other end of the primary to the series connected resistors R7 and R9 and this resistor divider provides DC bias to the base of transistor Q3 as well as oscillator feedback. Emitter resistor R10 provides inverse current feedback. Diodes CR1 and CR2 are connected back-to-back at the base of transistor Q3 so that forward diode voltage drop limits the feedback voltage to approximately 1½ volts peak to peak. The DC blocking capacitor C3 is utilized because the diodes are connected to the base with several volts DC bias potential. Resistor R8 is connected from the other side of capacitor C3 and the series combination of resistor R8 and capacitor C3 have little effect upon the circuit operation unless and until a feedback current is applied. Feedback current applied from the hand-probe drive transformer permits frequency or phase synchronization independent of the amplitude limiting action which diodes $CR_1$ and $CR_2$ apply to the oscillator circuit. The result is that fewer intermodulation products are created so that there is less tendency to lock in on the odd and unwanted frequencies generated by the crystal vibrations. The result is that the handpiece 22 and needle 33 will operate at a precise preselected frequency as chosen by tuning knob 57, (FIG. 8) and the consequent position of the core 24 of transformer T2. Redundent high ohmic grounded shield 29 is connected to plug 29a which fits into grounded plug 28b.

Feedback is applied through R-lock resistor R16 which is a relatively high resistance from a point on the output transformer T1 which adequately reflects the resonant impedance of the ultrasonic motor crystals in the handpiece 22 in use. An elapsed time indicator meter 108 illustrated in FIG. 13 may also be connected to plug J4 to indicate the total time the device has been utilized, i.e. tissue exposure time.

The handpiece 22 is one of the main areas of invention herein in that the design approach of the present invention is unique since in the present invention the critical matching is accomplished by working backwards wherein first the natural resonant frequency of the tool to be vibrated is found—whether it be a needle, rod or knife which is selected by the surgeons. Thus the surgeon can specifically decide in advance what size operating tool he desires rather than being required to use a tool which has its size and weight established by other type specialists.

In the case of cataract needles, for example, doctors desire to use 19 gauge, 21 gauge and 23 gauge needles about 1 inch in length with the largest aspiration hole possible in all cases. Once these dimensions of the needles are specified, the complete design is already determined. Since as shown in FIG. 1A, these needles would have to be one-half wave length under existing art, a 1 inch needle with an end piece for fastening would if made of steel require a frequency of operation approximately 25 KHz. Such a state of the art unit is illustrated in FIG. 5A wherein the needle and impedance transformer 81 and 82 respectively are each about 10.36 cm in length and are mated together by a threaded shaft 84 which is received in an internally threaded portion 83 of needle 81. The motor 86-32-87 may be about 10.36 cm and the overall length of the combination would be about 12 inches.

Since the motor 86-32-87 can be designed utilizing 304-Austenic stainless steel for the rear piece 86 lead-zirconatetitanate for the crystals 32 and titanium for the front piece 87 and, such a motor could be designed to oscillate longitudinally at the frequency of the actual tool to be used. If, for example, the tool 81 naturally resonated at 32.8 KHz a one-half wavelength motor could be designed to also oscillate at 32.8 KHz but the needle would not be 1 inch long. For this particular mode using our techniques a design can be calculated within 1/10 of 1% of specifications which means that the device will operate within 33 cycles of the design specifications. Our motors have a low Z and a low Q with an efficiency of 92% in converting from electrical to vibratory energy.

Once the motor 86-32-87 has been designed, a one-half wave exponential or other type geometric horn 82 also made of titanium can be designed and high efficiencies are obtained. The motor 86-32-87 and the horn 82 are assembled by utilizing the threaded shaft 34 at which time the basic vibrator is thus produced. Such motors comprise a single full wave motor/horn combination operating at the same frequency as the selected operating tool such as a needle. Utilizing such straight forward overly simplified design as described above gives rise to several disadvantages however, 1. The unit becomes too long.
2. The motor tends to vibrate the tool tip loose since they are joined at a antinodal vibrating maximum point.
3. An extra part is required to lock-up the needles, knives and other tools to the horn drastically mistuning the vibratory system.
4. Water cooling is usually needed due to the high inefficiency which appears as heat.

On the other hand, if the generator frequency is simply shifted to rematch the change in conditions due to bad designs, less power will be fed into the instrument, there will be more heating and a shifting of the oscillating frequency every time the load is changed by application even slightly, will take place.

The present invention uniquely solves these problems by completely eliminating the needle, knife or other tool as a separate entity and by constructing it actually as a part of the front impedance transformer (the horn) as shown as in FIGS. 4A, 4B, 6A and 6B. This results in the following distinct advantages.

Figure 6A:
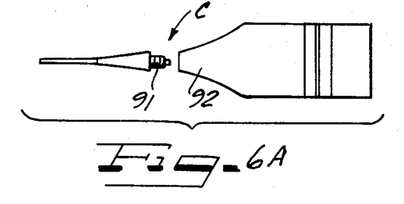
FIG. 6A illustrates our superior modification of the invention and shows the needle and frontpiece as a total of λ/2 wave instead of a full wave.
Figure 6B:
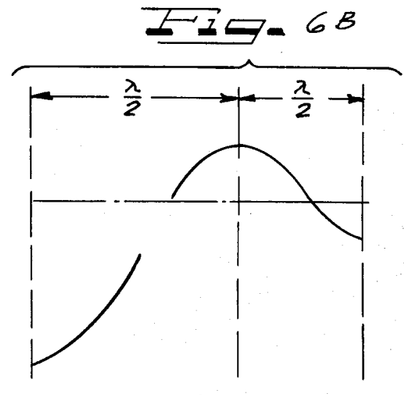
FIG. 6B is a plot of vibratory amplitude against physical distance. (Note, use of 2 half-waves and the far greater amplitude at the needle tip The needles—or tool—becomes part of the frontpiece design.

1. The overall length is shortened to a highly desirable length for easy manipulation.
2. The coupling joint C comprising the coupling between the horn 92 and the needle 33 can be moved closer to a "null" point eliminating any tendency of the tool to become unscrewed due to the severe antinodal vibrations i.e. it is not an antinode but a node.
3. Any excess mass in the form of "bosses", ridges, etc., which seriously mistunes the needles, knives, or the entire system are eliminated.
4. The power transfer is increased by 300%.
5. The need for circulating water for cooling is eliminated.

In the case for all gauges of needles, rods, tubes, et al, the exponential equation below applies:

$$S = S_0 \epsilon^{-\gamma \lambda} \qquad \text{Where: } \gamma = \text{Taper Factor} \\ \lambda = 2\pi$$

Where $\gamma$ is the taper factor. It can be shown that once the large diameter $D_1$ and the small diameter $D_2$ are chosen, the overall length L of the horn is uniquely determined for any given frequency and material thereafter selected in accordance with the above equation. Thus, the length L and the diameters $D_1$ and $D_2$ are chosen and the rest of the horns dimensions are automatically and completely fixed. The diameter of the needle and its desired length are selected first and all of the needed fabrication data is thereby established.

The selection of the breakpoint C illustrated in FIG. 6A and in FIGS. 7A through 7F is selected to be close to the node of vibration an antinode while the surface of contact area thereat is selected to be adequate to the power required to be transmitted. Once these are chosen the tool design is complete.

Figure 4B:
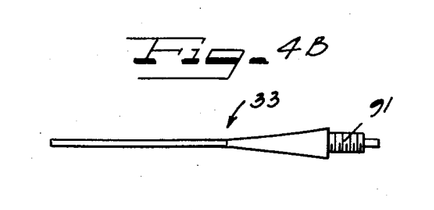
FIG. 4B illustrates an actual working tip of the invention; in this case a hollow needle.
Figure 4C:
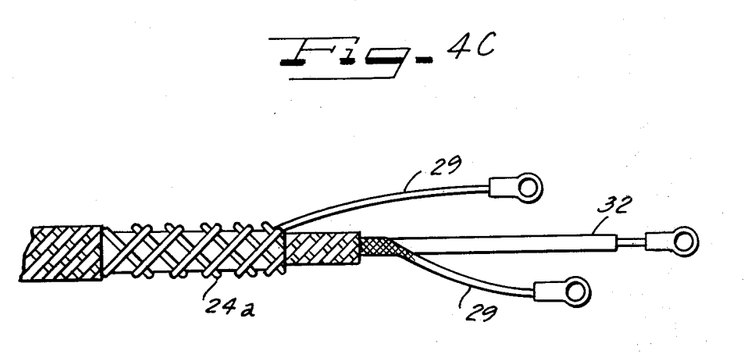
FIG. 4C illustrates the cable for the tool piece of FIG. 4A.

FIG. 4A and 4B illustrate in partial breakaway the unique hand tool of the invention.

Figure 7A:
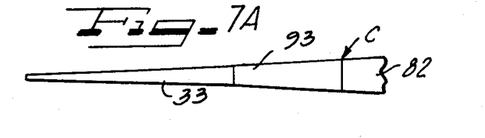
FIGS. 7A–F illustrate a rod, osteotome, cannula and several knives including a Graefe knife for use with the invention When properly redesigned, all become part of the front λ/2 piece.
Figure 7B:
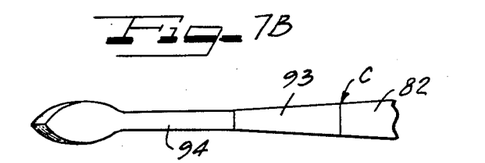
Figure 7C:
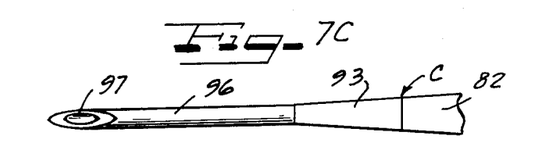

FIGS. 7A through 7F illustrate different instruments and tool designs that can be used with the invention with FIG. 7A showing a tapered rod 33 connected to a transition portion 93 which is connected to the rod by brazing. FIG. 7B illustrates an osteotome 94 connected to a similar transition portion 93. FIG. 7C illustrates a hollow needle 96 with a ground-off point 97 similarly connected to the tapered transition portion 93. FIG.

Figure 7D:
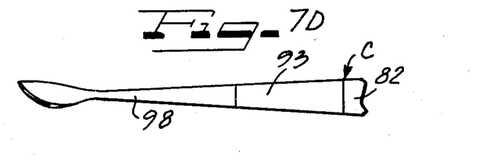
Figure 7E:
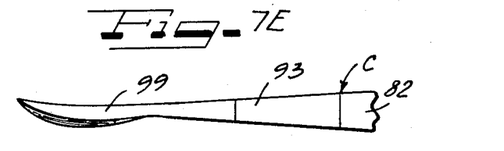
Figure 7F:
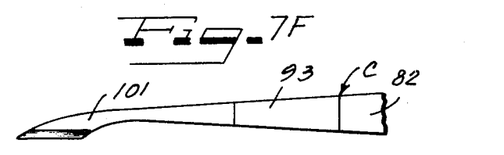

7D illustrates a microsurgery knife 98 connected to the transition portion 93. FIG. 7E illustrates a Graefe knife 99 connected the transition portion 93 and FIG. 7F illustrates a Girard cataract knife 101 connected to the transition portion 93. Since some of these devices have different shapes their natural frequency of resonance is first obtained using geometry and a computer and the natural frequency of vibration thereby calculated. Tests can then be conducted at that particular frequency and corrections made if necessary. Errors can be corrected for by making change in the horn portion quite readily.

We have discovered that for successful transfer of maximum energy and proper operation each component part of the unit—such as the needle in the tool—the horn or the motor must not be compromised in their design and each separate part must be designed to an exact frequency to prevent mismatch heating and loss of output power. Although the generator unit 105 of the invention can readily be adjusted from 28 to 58 KHz by merely adjusting the tuning slug position of the inductor core with knob 57, the indiscriminant application of a different merely peaking frequency will force the motor/horn/tool combination to operate at some compromise and in effectual frequency seen though the system is resonant. On the other hand, if proper design techniques according to this invention are utilized, medical tools can be constructed which operate within 1% or better of the design frequency which in addition to having the high efficiency of energy transfer allows ready replacement and field interchange of standardizable parts and even more important assures that all of the parts will operate in the desired safe mode and at the power setting required for a specific operation whose power has been set previously.

Systems of the prior art have invariably encountered difficulty in assuring that single mode operation of magnetostriction and cylindrical PZT units occur and it is common for transverse modes sometimes called "Killer Modes" to be readily set up in the operating needles, knives and tools. As shown in FIG. 15 a needle can whip violently over ¼ of an inch or more when inside the eye if the transducer goes into one of these odd vibratory modes; a condition which is very dangerous and injurious to the patient.

For these reasons as well as others the design of our invention is unique and the apparatus is built as an overall system which it is desired to patent as such with each of the components individually designed for optimum performance with each other. In our design if two out of three of the parts were capable of going into the vibratory "Killer Mode" it would still require four parts to do so simultaneously for this to happen. This invention therefore assures that the vibratory "Killer Mode" cannot exist because:

1. The needle is scientifically designed so as to specifically prevent transverse "moding".

2. The horn is also designed so that it will not permit transverse moding. (The critical motor with the untuned PZT crystals in it thus, will never see a sympathetic ambience even though it is capable of vibrating in three distinct major modes.)

3. The generator of the present invention is designed (due to the high feedback control of all its oscillator parts) so as to be strictly in its frequency peregrinations over a very narrow range.

Thus, the present invention completely prevents any onset of "Killer Mode" vibration by highly unique design of the tools and all parts substantially increasing the safety to the patient over all systems of the prior art.

It can be seen that this invention comprises the unique concept of first selecting the particular tools desired to be used by a surgeon, for example, and then designing a transition piece, a horn and a motor so that all three elements of the combination are tuned to the frequency of the medical tool selected and which is the one utilized during the actual operation. The frequency of the system can then be set by adjusting the knob 57 (FIGS. 8 & 11) to move the core tuning element of the transformer T2 to the known frequency, then the power into hand instrument unit 22 can be selected by pushing the proper switch Sa1 through Sa6 to assure that the desired power is available. Due to the unique system design the hand instrument will not change mode of vibration due to change in power levels at will or to loading of the worktip.

Suction is applied to the end of the hollow type needles through the center of the workpiece and the tubing conduit 103 illustrated in FIG. 4A so as to remove all tissue which has been broken by penetration and reduced into small pieces by micro-streams as shown in FIG. 21. The use of an angle theta ($\theta$) illustrated in FIGS. 20 and 21 of precisely 37½° results in optimum breakup and removal of the material.

Although this invention has been described with respect to preferred embodiments it is not to be so limited as changes and modifications may be made which are within the full intended scope as defined by the appended claims.

We claim as our invention:

1. An ultrasonic medical instrument comprising an ultrasonic oscillator, a handpiece, an ultrasonic motor mounted in said handpiece and electrically connected to said ultrasonic oscillator, a tool and transition horn connected to said ultrasonic motor and the combination having a wave length equal to $n\lambda/2$ where $n$ is an integer and $\lambda$ is the wave length of the operating frequency of said motor and wherein a portion of said tool is tapered to mate with said geometry of the transition horn so as to prevent mismatch and is a continuous extension of said horn, and wherein said internal ultrasonic motor consists of a cylindrical rear piece of steel, lead-zirconate-titanate crystals mounted adjacent one end of said rear piece and a front piece of titanium mounted adjacent said crystals and having a portion which is geometrically tapered, and said tool formed with a taper such that its diameter at the connection point to said front piece is the same as the end of said front piece.

2. An ultrasonic medical instrument according to claim 1 wherein said handpiece is directly covered by electrically insulating plastic material, providing insulation but not loading or mismatch.

3. An ultrasonic medical instrument according to claim 1 wherein said tool is formed of stainless steel or titanium.

4. An ultrasonic medical instrument according to claim 1 wherein said tool comprises a hollow needle and suction means connected to said needle.

5. An ultrasonic medical instrument according to claim 4 wherein the end of said needle is tapered at an angle in the range between 30° to 40° with the longitudinal axis of said needle.

6. An ultrasonic medical instrument according to claim 4 wherein the end of said needle is tapered at an angle of 37½° with the longitudinal axis of said needle.

7. An ultrasonic medical instrument according to claim 1 wherein said ultrasonic oscillator is electrically connected to said ultrasonic motor by at least two electrical conductors, one of which is a zero ohmage ground.

8. An ultrasonic medical instrument according to claim 7 wherein a second low, but not zero, ohmage ground is electrically connected between said ultrasonic motor and said ultrasonic oscillator as a safety connection and indicator of failure.

9. An ultrasonic medical instrument according to claim 8 wherein said second ground is of appreciable resistance say 8 ohms so as to maintain ground but cut operating power to the tool drastically should any operation be attempted via this means.

10. An ultrasonic medical instrument according to claim 1 wherein said oscillator includes means for changing its frequency over a controlled range so as to match the motor, transition horn and operating tool but prevent odd moding.

11. An ultrasonic medical instrument according to claim 9 wherein means are provided for varying the output power of said oscillator to said motor tool combination.

12. An ultrasonic medical instrument according to claim 1 wherein said oscillator includes a transistor with a base circuit and a feedback resistor connected between said motor and the base circuit of said transistor in a configuration which locks the oscillator at the resonant frequency of said motor tool combination.

13. An ultrasonic instrument according to claim 1 wherein said handpiece is completely encapsulated in molded rubber so as to provide a protective sheath permitting high temperature auto claving of said workpiece and also eliminating all transfer of random energy to the user and which eliminates the need for all cooling water while still providing comfort to the user.

14. An ultrasonic instrument according to claim 1 including in said handpiece an aluminum high voltage center electrode, said front piece providing a favorable high to low mass ratio for increased motion at the working end as an exponential horn of the shape defined by the equation:

$$S = S_0 E^{-\gamma \lambda}$$ Where: $\gamma$ = Taper Factor $\lambda = 2\pi$ and the diameter of the motor being $D_1$ and the end diameter of the actual tooltip being $D_2$ thus making the tooltip mathematically and physically part of the motor/horn combination.

15. An ultrasonic instrument according to claim 14 wherein said tool forms and comprises an innate part of an exponential horn, a selectable variety of needles, rods, cannulae, knives and assorted other types of surgical tips, thereby making these devices part of the tip and of the ultrasonic electro-mechanical system, said surgical tips threadedly connected close to an antinode low level vibrating point of the horn itself eliminating any tendency to vibratory loosening and thereby loss of full transfer of the energy available to said tool.

16. An ultrasonic instrument according to claim 15 wherein said tools comprise either a needle, rod or knife on one end and a partially incomplete ultrasonic horn design on the other end and threadedly fastened to the remaining partially tapered ultrasonic horn distending as part of the motor/horn combination so as to be securely fastened causing bearing contact of a high standard ground surface caliber mating over its annular area of at least 90%.

17. An ultrasonic medical instrument comprising an ultrasonic oscillator, a handpiece, an ultrasonic motor mounted in said handpiece and electrically connected to said ultrasonic oscillator, a tool and transition horn connected to said ultrasonic motor and the combination having a wave length equal to $n\lambda/2$ where $n$ is an integer and $\lambda$ is the wave length of the operating frequency of said motor and wherein a portion of said tool is tapered to mate with said geometry of the transition horn so as to prevent mismatch and is an extension of said horn, wherein said internal ultrasonic motor consists of a cylindrical rear piece of steel, lead-zirconate-titanate crystals mounted adjacent one end of said rear piece and a front piece of titanium mounted adjacent said crystals and having a portion which is geometrically tapered, and said tool formed with a taper such that its diameter at the connection point to said front piece is the same as the end of said front piece, and wherein the connection point between said tool and said transition piece is essentially a nodal point.

18. An ultrasonic instrument according to claim 17 wherein an exponential transformer is physically part of the front of the motor which is divided at a point midway along the horn taper at approximately a nodal point about $\lambda/4$ wave length with the half toward the motor being metal and not broken at a maximum vibrating point while the other part of a transformer section is the tool plus another piece of said transformer.

19. An ultrasonic instrument according to claim 17 including a pre-biasing stressing center bolt of titanium having a central bore hole and having an upper limit on the diameter of the central bore hole and concomitantly the size of the hollow needle to be used with a given size handpiece said bolt connecting portions of said motor.

20. An ultrasonic instrument according to claim 17 wherein said tool vibrates only in the longitudinal mode thus providing superior penetration by the inertial interacting of its metal tip and compliant tissue materials and which additionally provides intense highly effective microstreaming forces for complete dissolution of the fragmented particles broken up by said penetration.

21. An ultrasonic instrument according to claim 20 wherein said tool is subjected to extremely high accelerating forces entailed by its unique construction so as to achieve a force of 72,000 G's at its extreme tip, thus penetrating tissue, cartilage or bone with ease while maintaining its own integrity and having long life.

22. An ultrasonic instrument according to claim 21 wherein said tool produces a powerful entrapment geometry creating circulating forces for complete dissolution of the fragmented particles entailed by use of a 37½° ground angle on the needles and rods.

23. An ultrasonic instrument according to claim 22 wherein said handpiece includes an embedded externally and internally threaded Teflon tubing connected to another Teflon fitting by a removable Silicone or medical grade plastic or rubber tubing screw.

24. An ultrasonic instrument according to claim 17 wherein said handpiece contains a readily disassembled aspiration tubing system made of high temperature materials such as Teflon and silicone rubber that can be quickly taken down, cleaned, sterilized and/or replaced without creating leaks in a low vacuum system usually used with such equipment.

25. An ultrasonic instrument according to claim 17 wherein said workpiece includes two distinct grounding systems one of conventional low ohmic resistance and the other utilizing a second, outer, stranded metallic shield of a slightly higher ohmic resistivity; specifically of 8 ohms.

26. An ultrasonic instrument according to claim 17 including an ultrasonic energy generator containing a lock-on oscillator connected to said motor, a mechanical preventive oscillator excursion control for tuning through a safe operating range, a push-button power control which does not change tuning as its power levels are changed, and a readily discernible neon-eye tuning indicator mounted on said oscillator.

27. An ultrasonic instrument according to claim 26 including a true reading ultrasonic wattmeter capable of accurately reading the ultrasonic power input into the workpiece itself connected to said instrument.

28. An ultrasonic instrument according to claim 26 including a sound indicator buzzer with level adjust control which operates when an operating footswitch is activated giving the operator an indication of the presence of ultrasonic energy.

29. An ultrasonic instrument according to claim 26 including a mechanically mounted inductor whose mechanical travel is limited by stops at either end to proscribe the range over which said oscillator is permitted to operate preventing frequencies of a dangerous nature to be produced.

30. An ultrasonic instrument according to claim 26 including a tuning indicator utilizing a neon light connected to said oscillator and a voltage across said light would be set to provide gas striking voltage at all conditions but is permitted to discernibly decrease without quenching when the output circuit resonates with the handpiece, said indicator being an exact and satisfactory indication of workpiece operation regardless of the tip used.

31. An ultrasonic instrument according to claim 26 wherein said oscillator in addition to the proscribed mechanical tuning arrangement contains a normal feedback means for sustaining oscillation and not requiring a unique sensor on the motor unit, said oscillator consisting of transistors operating in a class A continuously conducting condition and Zener diodes being used to limit the oscillator voltage amplitude resulting in more stable operation, as voltage levels and frequencies are relatively independent of power supply variation thus making the oscillator work correctly regardless of the setting of the push-button switch wherein normally it would not be possible.

32. An ultrasonic instrument according to claim 31 wherein a combination of resistors and capacitors are connected to the controlled oscillator which have little effect upon an earlier preset frequency and phase synchronization independently of the amplitude limiting action resulting in the correct operation of each circuit independently yet conjointly producing few intermodulation products thereby creating "lock-in" of unwanted dangerous odd-mode frequencies.

33. An ultrasonic instrument according to claim 26 wherein said ultrasonic generator which includes a relatively high or "R-Lock" resistor of relatively high resistance for receiving the feedback voltage variation caused by the frequency shift signaling from the workpiece transformer back to the oscillator circuit thereby reflecting the impedance changes of the handpiece into the oscillator.

34. An ultrasonic instrument according to claim 26 including an elapsed time indicator connector circuit for reading the cumulated intermittantly applied ultrasonic power utilized by operation during any single operation.

* * * * *